(12) United States Patent
Bittman et al.

(10) Patent No.: US 6,613,748 B2
(45) Date of Patent: Sep. 2, 2003

(54) C-GLUCOSYL ETHER LIPIDS

(75) Inventors: Robert Bittman, Rosyln Heights, NY (US); Gilbert Arthur, Winnepeg (CA); Richard W. Frank, Riverside, CT (US)

(73) Assignees: The Research Foundation of the City University of New York, New York, NY (US); The University of Manitoba, Winnipeg (CA)

(*) Notice: Subject to any disclaimer, the term of this patent is extended or adjusted under 35 U.S.C. 154(b) by 43 days.

(21) Appl. No.: 10/011,781

(22) Filed: Dec. 11, 2001

(65) Prior Publication Data

US 2002/0128214 A1 Sep. 12, 2002

Related U.S. Application Data

(60) Provisional application No. 60/254,598, filed on Dec. 11, 2000.

(51) Int. Cl.$^7$ ............... A61K 3/7008; A61K 31/70; A61K 5/06

(52) U.S. Cl. ............... 514/42; 514/62; 536/18.7; 536/53; 536/55.2; 536/120

(58) Field of Search ............... 514/42, 62; 536/18.7, 536/53, 55.2, 120

(56) References Cited

U.S. PATENT DOCUMENTS

| | | |
|---|---|---|
| 4,920,016 A | 4/1990 | Allen et al. |
| 5,219,845 A | 6/1993 | Salari et al. |
| 5,369,097 A | 11/1994 | Salari et al. |
| 5,385,685 A | 1/1995 | Humphreys et al. |
| 5,409,902 A | 4/1995 | Carson et al. |
| 5,506,217 A | 4/1996 | Salari et al. |
| 5,756,774 A | 5/1998 | Bittman et al. |

FOREIGN PATENT DOCUMENTS

| | | |
|---|---|---|
| EP | 142333 | 5/1985 |
| WO | WO 97/11707 A | 4/1997 |

OTHER PUBLICATIONS

Yang et al., Organic Letters, (1999), vol. 1, No.13, 2149–2151.*

Yang, Guangli et al., "Synthesis and Growth Inhibitory Properties of Glucosamine–Derived Glycerolipids;" Organic Letters, vol. 3(2):197–200 (2001); American Chemical Society, Columbus, Ohio.

Erukulla, R. K. et al.; "Synthesis and Evaluation of the Antiproliferative Effects of 1–O–Hexadecyl–2–O–methyl–3–O–(2'–acetamido–2'–deoxy–βD–glucopyranosyl)–sn–glycerol and 1–O–Hexadecyl–1–2–O–methyl–1–3–O–(2'–amino–2'–deoxy–β–D–glucopyranosyl)–sn–glycerolon Epithelial Cancer Cell Growth," J. Med. Chem., vol. 39:1545–1548 (1996), American Chemical Society, Columbus, Ohio.

Yang et al., "Convergent C–Glycolipid Synthesis via the Ramberg–Backlund Reaction: Active Antiproliferative Glycolipids," Organic Letters, vol. 1:2149–51 (1999), American Chemical Society, Columbus, Ohio.

Adam et al., "A new class of potent antiproliferative glycolipids" Chemistry and Physics of Lipids, 59, 255–261 (1991) Elsevier Science , Oxford, United Kingdom.

Bauer et al., "Zur stereoselektiven Synthese von 1–O–Alkyl–3–O–benzyl–sn–glycerolen und 1–O–Alkyl–2–O–methyl–3–O–β–D–glycosyl–sn–glycerolen" Liebigs Ann., Stet , 765–768 (1991), Elsevier Science, Oxford, United Kingdom.

Bittman et al., "Glycosylated Antitumor Ether lipids: Synthesis and Growth–Inhibitory Properties", Abstract Book XIXth International Carbohydrate Symposium, Univ of California, San Diego, USA Aug. 9–14 (1988), Elsevier Science, Oxford, United Kingdom.

Lu et al. "The αand βanomers of 1–O–hexadecyl–2–O–methyl 1–3–S–thioglucosyl–sn–glycerol inhibit the proliferation of epithelial cancer cell lines", Oncol. Rep. vol. 1: 933–96 (1994), Elsevier Science, Oxford, United Kingdom.

Salari et al. "Inhibition of protein kinase C by ether–linked lipids is not correlated with their antineoplastic activity on WEHI–3B and R6X–B15 cells", Biochem Biophys. Acta. vol. 1134(1): 81–88 (1991.), Elsevier Science, Oxford, United Kingdom.

Weber et al. "Synthesis of Ether Glyceroglycolipids", Chem. Phys. Lipids, vol. 41: 93–100, (1996), Elsevier Science, Oxford, United Kingdom.

Byun et al. "A Short Synthesis of Antitumor Ether Thioglycolipids: Thioglycosidation of a Glucose Donor with a Tributylstannyl Sulfide Acceptor" Tetrahedron Letters, vol. 36(29): 5143–5146, (1995), Elsevier Science, Oxford, United Kingdom.

(List continued on next page.)

Primary Examiner—Samuel Barts
Assistant Examiner—Michael C. Henry
(74) Attorney, Agent, or Firm—Burns, Doane, Swecker & Mathis LLP

(57) ABSTRACT

A C-glucosyl ether lipid of the following formula:

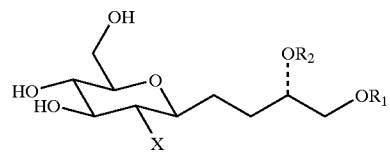

wherein $R_1$ is a $C_{12}$–$C_{20}$ alkyl or $C_{12}$–$C_{20}$ alkenyl; $R_2$ is a $C_1$–$C_3$ alkyl or $C_3$ cycloalkyl; and X nitrogen-containing group.

16 Claims, 9 Drawing Sheets

OTHER PUBLICATIONS

Kumar et al. "Preparation of Ether–linked 2–Acetamido–2–deoxy–β–Glycolipids via Zinc Chloride Promoted Coupling of $Ac_4GlcNAc$–Cl with Lipid Hydroxy Groups", Tetrahedron Letters, vol. 35(4): 505–508, (1994), Elsevier Science, Oxford, United Kingdom.

Weber et al. "Metabolism of ether glycolipids with potentially antineoplastic activity by Ehrlich ascites tumor cells" Biochem. Biophy. Acta., vol. 959: 91–94, (1988), Elsevier Science, Oxford, United Kingdom.

Gregory Gregoriadis, Ph.D. "Incorporation of Drugs, Proteins, and Genetic Material" Liposome Technol., vol. 2: 19–31, (1984), CRC Press, Boca Raton, Florida.

Guivisadalsky et al., "Syntheisis and Antineoplastic Properties of Ether–Linked Thioglycolipids" J. Med. Chem., 33: 2614–2641 (1990), Journal of Medicinal Chemistry American Chemical Society, Columbus, Ohio, USA.

* cited by examiner

C-GLUCOSYL ETHER LIPIDS

The U.S. Government has a paid-up license in this invention and the right in limited circumstances to require the patent owner to license others on reasonable terms as provided for by the terms of GM 51216 and RR 03037 awarded by the National Institutes of Health.

FIELD OF INVENTION

This invention relates to C-glucosyl ether lipids, including their synthesis and use.

BACKGROUND OF THE INVENTION

The study of C-glycoside analogs of bioactive O- and N-glycosides is a mature field. In addition to the focus on their structural and conformational properties as probes for the importance of the anomeric and exo-anomeric effects, the significance of C-glycosides is that they are essentially inert to degradation because the anomeric carbon has been transformed from a hydrolytically labile O- or N-acetal link to an ether linkage. The underlying assumption for the use of C-glycoside analogs in glycobiology is that the conformational differences between the O- (or N)-linked natural material and the C-linked analog will be minimal. The corollary to the minimal difference hypothesis is that the recognition and binding of the C-analog will be similar to that of the natural material.

In contrast to the large number of C-glycosides that have been synthesized, there have been surprisingly few direct O vs. C biological activity comparisons. The most thorough comparison was done for the C-lactose O-lactose case reported in significant papers in 1995, 1996, and 1998 by the Kishi and Schmidt and Jiminez-Barbero groups, who focus on nuclear Overhauser enhancement data and modeling results. There is partial but not complete agreement as to the similarities and differences in the conformation of ground-state and of binding conformations. Espinosa, et al., *J. Am. Chem. Soc.*, 118:10862–10871 (1996); Espinosa, et al., *J. Am. Chem. Soc.*, 120:1309–1318 (1998); Wei, et al., *J. Org. Chem.*, 60:2160–2169 (1995); Ravishankar, et al., *J. Am. Chem. Soc.*, 120:11297–11303 (1998). Recently, we reported a comparison between an antiproliferative 2-deoxyglucosyl glycerolipid (compound 1) and its exact C-analog (compound 2) where the C-glycoside showed a several fold weaker activity. Yang, et al., *Org. Let.*, 1:2149–2151 (1999).

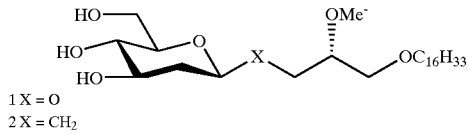

1 X = O
2 X = CH$_2$

Although C-glycosylamino compounds have been prepared (Gaurat, et al., *Tetrahedron Lett.*, 41:1187–1189 (2000)), there has been no previous preparation of a lipid that is coupled to a C-glycoside in which glucosamine is the parent carbohydrate. It is also noted that direct methods for making C-glycosides having 2-amino groups are recognized as being especially difficult to achieve "because of the incompatibility of neighboring nitrogen-based functional groups ... with common glycosylation strategies" (Bertozzi et al., *J. Org. Chem.* 1996, 61, 6442–6445).

SUMMARY OF THE INVENTION

Briefly, the invention relates to a C-glucosyl ether lipid of the following formula:

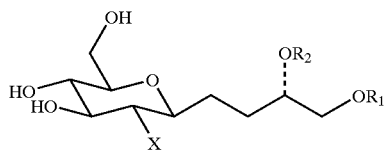

wherein $R_1$ is a $C_{12}$–$C_{20}$ alkyl or $C_{12}$–$C_{20}$ alkenyl; $R_2$ is a $C_1$–$C_3$ alkyl or a $C_3$ cycloalkyl; and nitrogen containing group. $R_1$ is preferably $C_{16}H_{33}$ or $C_{18}H_{37}$, $R_2$ is preferably a $C_1$–$C_3$ is preferably NH$_2$, NHCOR$_3$ or NHSO$_2$R$_4$, wherein $R_3$ is a $C_1$–$C_3$ alkyl, and $R_4$ is a $C_1$–$C_3$ alkyl phenyl, a substituted phenyl or a substituted naphthyl. More preferably, X is NH$_2$, $R_1$ is $C_{16}H_{33}$ and $R_2$ is CH$_3$. The invention also relates to a pharmaceutical composition containing the C-glucosyl ether lipid defined in the formula, as well as a method of treating an animal afflicted with cancer by administering a anti-cancer effective amount of the pharmaceutical composition.

The invention likewise relates to a method of synthesizing C-glucosyl ether involving a) synthesizing an ether lipid having an sn-2 carbon and an O-alkyl or O-cycloalkyl side chain attached to the sn-2 carbon; b) sulfur-linking a glucose derivative to the ether lipid synthesized in step a) to form a thioglycoside intermediate, the glucose derivative having a nitrogen containing group at the C2 position; and c) converting the thioglycoside intermediate to a C-glucosyl ether lipid via a Ramberg-Bäcklund rearrangement.

DETAILED DESCRIPTION OF THE INVENTION

Figure 1:
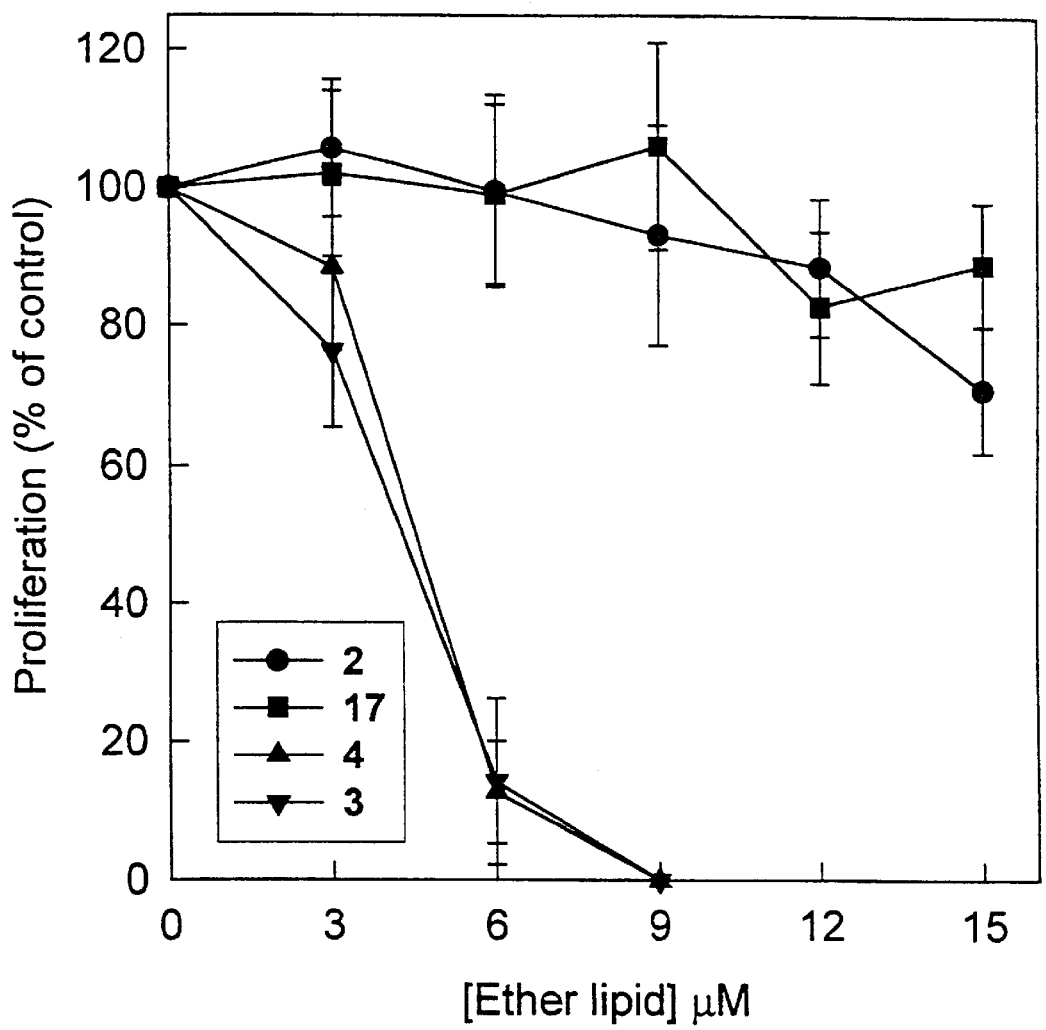
FIG. 1 is a graphical depiction of the results of an anti-proliferation evaluation of two compounds in accordance with the invention (compounds 17 and 4) and two comparative compounds against the neuroblastoma cell line SK-N-MC.

We have synthesized and tested new C-glucosyl ether lipids which surprisingly exhibit in vitro anti-proliferative effects similar to O-glucosyl analogs. This result is surprising in light of our previous work in which the C-analog of 2-deoxyglucosyl glycerolipid showed a several fold weaker activity than 2-deoxyglucosyl glycerolipid itself (Yang et al., Org. Lett., 1:2149–2151 (1999)). It is believed that the anti-cancer efficacy of the present C-glucosyl ether lipids in vivo would be superior to that of the O-glucosyl analog because of the resistance of C-glucosyl compounds to breakdown by glycosidases.

As described above, C-glucosyl ether lipids in accordance with the invention have the formula:

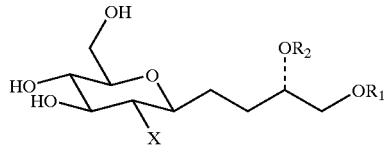

wherein $R_1$ is a $C_{12}$–$C_{20}$ alkyl or $C_{12}$–$C_{20}$ alkenyl; $R_2$ is a $C_1$–$C_3$ alkyl or a $C_3$ cycloalkyl; and X is a nitrogen containing group. $R_1$ is preferably $C_{16}H_{33}$ or $C_{18}H_{37}$, $R_2$ is preferably a $C_1$–$C_3$ alkyl; and X is preferably $NH_2$, $NHCOR_3$ or $NHSO_2R_4$, wherein $R_3$ is a $C_1$–$C_3$ alkyl, and $R_4$ is a $C_1$–$C_3$ alkyl, a phenyl, a substituted phenyl or a substituted naphthyl. More preferably, X is $NH_2$, $R_1$ is $C_{16}H_{33}$ and $R_2$ is $CH_3$. The terms "alkyl" and "alkenyl" include straight and branched hydrocarbon chains. In addition, a C-glucosyl ether lipid in accordance with the invention can be either an R or S enantiomer, or any combination of an R and S enantiomer.

The invention also relates to a pharmaceutical composition containing the C-glucosyl ether lipid defined above, as well as a method of treating an animal afflicted with cancer by administering a anti-cancer effective amount of the pharmaceutical composition. A "pharmaceutical composition" is any composition comprising the C-glucosyl ether lipid of the invention, or a pharmaceutically-acceptable salt or prodrug thereof, and a suitable, pharmaceutically-acceptable carrier, including liposomal formulations and other drug delivery vehicles/techniques. An "anti-cancer effective amount" of the pharmaceutical composition is any amount capable of slowing the rate of proliferation of a cancer in an animal.

We have also discovered a direct method of synthesizing the C-glucosyl ether lipids in accordance with the invention that avoids the problems created by the incompatibility of nitrogen-based functional groups with typical glycosylation strategies. Further, our method provides an essentially perfect stereoselectivity in every synthetic step. The method involves a) synthesizing an ether lipid having an sn-2 carbon and an O-alkyl or O-cycloalkyl side chain attached to the sn-2 carbon; b) sulfur-linking a glucose derivative to the ether lipid synthesized in step a) to form a thioglycoside intermediate, the glucose derivative having a nitrogen containing group at the C2 position; and c) converting the thioglycoside intermediate to a C-glucosyl ether lipid via a Ramberg-Bäcklund rearrangement

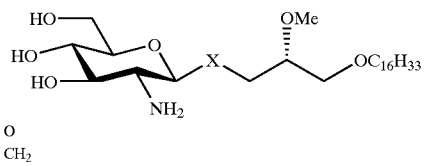

3 X = O
4 X = CH₂

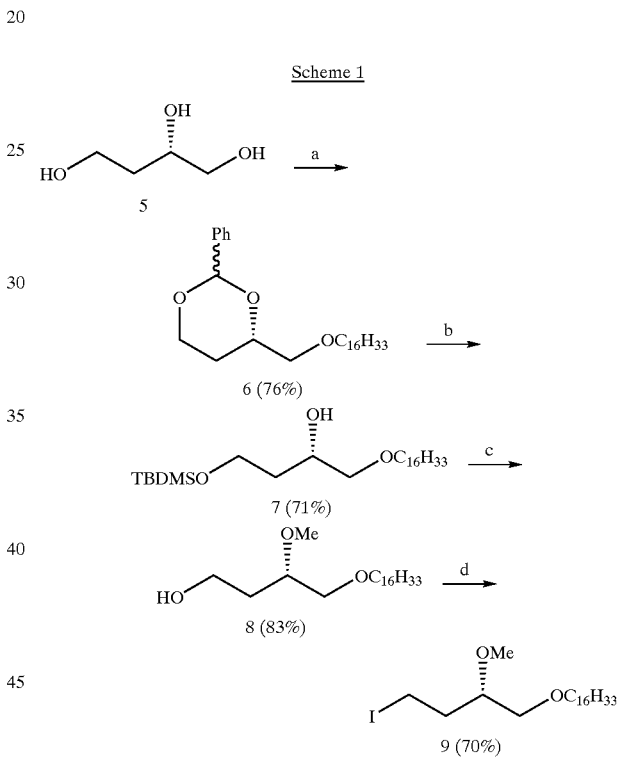

(a) (1) PhCHO, CH(OMe)₃, (2) NaH, Bu₄NBr, C₁₆H₃₃Br;
(b) (1) 80% AcOH, reflux, (2) TBDMSCl, CH₂Cl₂, imidazole;
(c) (1) NaH, MeI, THF, (2) Bu₄NF, THF;
(d) Ph₃P, I₂, imidazole, PhMe, reflux.

The general sequence of synthesis is similar to that of 2-deoxy-O-glycoside 3. In the 2-deoxyglycoside series, the methyl ether was introduced into the thioglycoside precursor via O-methylation of the side chain hydroxyl prior to the Ramberg-Bäcklund rearrangement. The corresponding methylation is not clean in the 2-acetamino glucose series because N-methylation also takes place. Therefore, we changed the sequence to synthesize the O-methyl side chain before making the thioglycoside. The synthesis of the lipid (S)-4-O-hexadecyl-3-O-methyl-1-iodobutane (9) was easily accomplished (Scheme 1) starting from (S)-1,2,4-butanetriol (5). This procedure is based on selective protection of 5 followed by O-alkylation. Deprotection using 80% acetic acid at reflux, followed by selective silylation of the primary alcohol afforded silyl ether 7. O-Methylation followed by deprotection using Bu$_4$NF proceeded to form primary alcohol 8. 4-O-Hexadecyl-3-O-methyl-1-iodobutane (9) was made from 8 and I$_2$/Ph$_3$P at reflux in toluene.

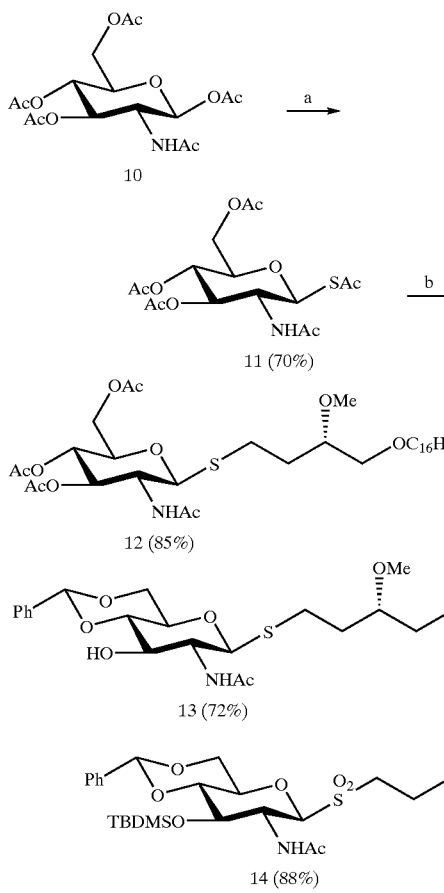

(a) (1) AcCl, (2) KSAc, acetone;
(b) NH$_2$NH$_2$·HOAc, DMF, Et$_3$N, 9;
(c) (1) guanidine, EtOH/CH$_2$Cl$_2$, (2) PhCH(OMe)$_2$, p-TsOH, DMF;
(d) (1) TBDMSCl, imidazole, DMF, (2) MMPP.

N-Acetyl-3,4,6-tri-O-acetyl-1-glucosamine-thioacetate 12 can be made from commercially available N-acetyl-D-glucosamine 10 in two steps (Scheme 2). See Horton, et al., *J. Org. Chem.*, 27:1794–1799 (1962), the pertinent portions of which are incorporated herein by reference. The S-acetate was selectively cleaved by NH$_2$NH$_2$. HOAc in DMF. Alkylation with iodide 9 in Et$_3$N gave thioglycoside 12 in good yield. See Park, et al., *Carbohydr. Lett.*, 1:179–184 (1995), the pertinent portions of which are incorporated herein by reference. Selective deprotection of the O-acetyl groups using guanidine (see Kunesch, et al., *Tetrahedron Lett.*, 28:3569 (1987), the pertinent portions of which are incorporated herein by reference) followed by benzylidene acetal protection of the 4,6-diol afforded thioglycoside 13. Treatment of alcohol 13 with TBDMSCl, followed by oxidation using MMPP, afforded sulfone 14. The Ramberg-Bäcklund rearrangement of sulfone 14 afforded alkene 15 (Z isomer only, which was confirmed by a nuclear Overhauser effect experiment) using 25% KOH on alumina in CBrF$_2$CBrF$_2$ at reflux in 78% yield (Scheme 3). We found that the yield of the reaction is much higher when freshly prepared KOH/Al$_2$O$_3$ is used rather than material that has been stored for one month in a desiccator.

The Ramberg-Bäcklund product 4 is much more stable than the Ramberg-Bäcklund product of a 2-deoxyglucose series. It can be stored at 0° C. for more than one month without any decomposition. Deprotection and reduction of alkene 15 using H$_2$ and 10% Pd/C afforded β-C-glycoside 16 in 85% yield. Of the several methods attempted for cleavage of the silyl group (e.g., Bu$_4$NF, formic acid, acidic ionic exchange resin, and BF$_3$, Et$_2$O conditions), only BF$_3$·Et$_2$O in CH$_3$CN gave a clean reaction (see King, et al., *Tetrahedron Lett.*, 36:4563 (1995), the pertinent portions of which are incorporated herein by reference). The N-acetyl group was cleaved by using 2 N KOH/EtOH at reflux at 120° C. to afford the final product 4.

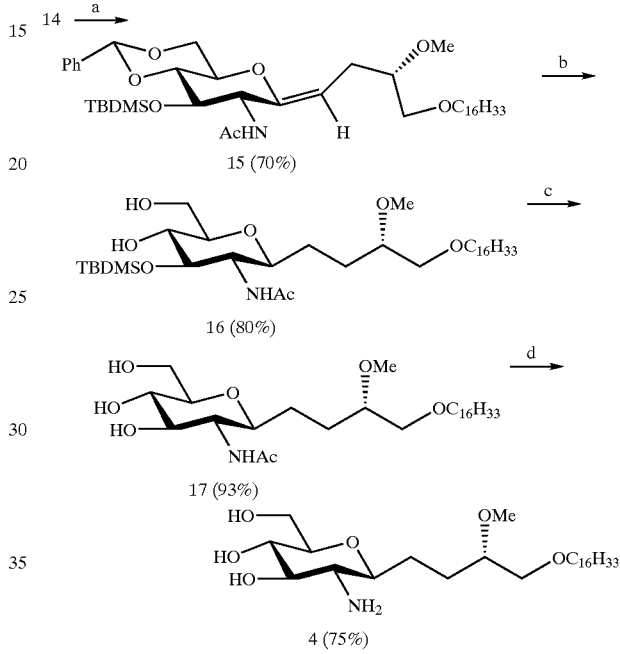

(a) CBrF$_2$CBrF$_2$, 25% KOH/Al$_2$O$_3$, t-BuOH, reflux;
(b) H$_2$, 10% Pd/C, EtOAc;
(c) BF$_3$·Et$_2$O, 0° C., CH$_3$CN;
(d) 2N KOH, EtOH, reflux.

Although a rather guarded outlook for the synthesis of C-glycosides of 2-amino sugars was expressed in 1996 (Roe, et al., *J. Org. Chem.*, 61:6442–6445 (1996)), several useful approaches have been reported (e.g., Gaurat, et al., *Tetrahedron Lett.*, 41:1187–1189 (2000); Junker, et al., *Tetrahedron Lett.*, 40:7063–7066 (1999); Cui, et al., *Carbohydr. Res.*, 309:319–330 (1998); Urban, et al., *J. Org. Chem.*, 63:2507–2516 (1998); Burkhart, et al., *Tetrahedron Lett.*, 39:255–256 (1998); Schafer, et al., *J. Org. Chem.*, 65:24–29 (2000); Xie, et al., *J. Carbohydr. Chem.*, 18:481498 (1999)). Unlike these approaches, however, our method provides essentially perfect stereoselectivity in every synthetic step, particularly in the Ramberg-Bäcklund sequence to afford exo glycal 16 and its reduction to afford the C-glycoside 15. Another advantage of our method is that the most rigorous conditions in our sequence involve the deacylation of 17 to afford the final product 4. A detailed description of an actual synthesis utilizing a method in accordance with the invention is provided in Example 1 below.

EXAMPLE 1

Synthesis (R)-2-Phenyl-(S)-4-hydroxymethyl-1,3dioxane. A sample of 2.60 g (20.6 mmol) of commercially available (Aldrich)

(S)-(−)-1,2,4-butanetriol 5, benzaldehyde (3.47 mL, 29 mmol), and trimethyl orthoformate (3.74 mL, 29 mmol) was dissolved in 80 mL of CH$_2$Cl$_2$, and 1 mL of CF$_3$CO$_2$H was added. After the reaction mixture was stirred for 24 hours at room temperature, the reaction was quenched by the addition of NaOMe (20 mg), diluted with 100 mL of ether, and filtered. After the filtrate was concentrated under reduced pressure, the residue was purified by column chromatography on silica gel, eluting with petroleum ether (PE)-EtOAc (5:1 to ~1:1) to afford 3.6 g (90%) of the product as a colorless oil. $^1$H NMR (300 MHz, CDCl$_3$) δ7.52–7.33 (m, 5H), 5.51 (s, 1H), 4.29 (dd, J=4.1, 10.7 Hz, 1H), 3.95 (m, 2H), 3.60 (m, 2H), 2.85 (s, 1H, OH), 1.85 (m, 2H). $^{13}$C-NMR (CDCl$_3$, 75 MHz): δ139.10, 129.58, 128.90, 126.85, 101.96, 78.35, 67.36, 66.29, 27.69.

(R)-2-Phenyl-(S)-4-hexadecyloxymethyl-1,3dioxane (6). To a suspension of NaH (3 g, 60% in mineral oil) in 30 mL of dry THF was added a solution of (R)-2-phenyl-(S)-4-hydroxymethyl-1,3-dioxane (1.47 g, 7.6 mmol) in 10 mL of THF at 0° C. After 30 min, hexadecyl bromide (3 mL, 9.88 mmol) and tetrabutylammonium iodide (0.28 g, 0.76 mmol) were added. After the mixture was stirred overnight, the reaction was quenched by addition of 5 mL of MeOH. The solvent was removed under reduced pressure, and ether and water were added. The product was extracted with ether. The organic layer was dried over Na$_2$SO$_4$ and concentrated. The product was purified by column chromatography on silica gel, eluting with EtOAc-PE (5%) to afford 1.55 g (50%) of 6 as a white solid; mp 51–54° C. MS: m/z 441 (M$^+$+Na$^+$), (calcd. for C$_{27}$H$_{45}$O$_3$, 418.662). $^1$H NMR (300 MHz, CDCl$_3$): δ7.51–7.31 (m, 5H, Ph), 5.54 (s, PhCH—), 4.32–4.27 (m, —CHO), 4.10–3.94 (m, 2H, —CH$_2$O—), 3.65–3.59 (m, 4H, —CH$_2$O), 1.89–1.83 (m, 2H, —CH$_2$—), 1.62–1.54 (m, 2H), 1.25 (s, 26H), 0.88 (t, 3H, CH$_3$). $^{13}$C-NMR (CDCl$_3$, 75 MHz): δ139.28, 129.32, 128.77, 126.79, 101.88, 77.09, 74.44, 72.61, 67.61, 32.74, 30.51, 30.30, 30.18, 29.18, 26.93, 23.51, 14.94.

(3S)-4-O-Hexadecyl-1,3-butanediol. Ether 6 (0.836 g, 2.0 mmol) was dissolved in 8 mL of 80% acetic acid at 90° C. The mixture was refluxed at this temperature for 1 hour, then quenched with NaHCO$_3$. The mixture was then extracted with Et$_2$O (3×30 mL). The organic layer was dried over Na$_2$SO$_4$ and concentrated in vacuo. The product was purified by column chromatography on silica gel, eluting with EtOAc-PE (50%) to afford 0.55 g (82%) of a white solid; mp 48° C. $^1$H NMR (300 MHz, CDCl$_3$): δ4.01 (m, 1H), 3.83 (q, 2H), 3.45 (m, 3H), 3.33 (m, 1H), 2.74 (d, J=5.9 Hz, 1H, OH), 2.55 (t, J=5.5 Hz, 1H, OH), 1.71 (m, 2H), 1.57 (m, 2H), 1.25 (s, 28H), 0.88 (t, J=6.2 Hz, 3H, CH$_3$). $^{13}$C-NMR (CDCl$_3$, 75 MHz): δ75.02, 71.86, 70.46, 61.25, 35.32, 32.22, 29.99, 29.77, 29.65, 26.42, 22.99, 14.41.

(3S)-4-O-Hexadecyl-1-O-tert-butyidimethylsilyl-3-butanol (7). To a solution of 4-O-hexadecyl-1,3-butanediol (0.50 g, 1.52 mmol) in 10 mL of CH$_2$Cl$_2$ was added TBDMSCI (0.259 g, 1.66 mmol), followed by imidazole (0.227 g, 3.33 mmol). The mixture was stirred at room temperature for 1 hour. The mixture was filtered and the filtrate was rinsed with CH$_2$Cl$_2$. The solution was concentrated and purified by column chromatography on silica gel (eluting with 20% EtOAc-PE) to afford 0.65 g (97%) of compound 7. H NMR (300 MHz, CDCl$_3$): δ3.97 (m, 1H), 3.82 (m, 2H), 3.47–3.34 (m, 4H), 3.11 (d, J=2.6 Hz, 1H, OH), 1.69 (m, 2H), 1.25 (s, 28H), 0.89 (m, 12H), 0.07 (m, 6H). $^{13}$C-NMR (CDCl$_3$, 75 MHz): δ75.17, 71.81, 69.69, 61.54, 35.92, 32.23, 29.99, 29.91, 29.78, 29.65, 26.43, 26.20, 22.99, 18.51, 14.41, −5.13.

4-O-Hexadecyl-3-O-methyl-1-butanol (8). To a suspension of 600 mg NaH (60% in mineral oil) in 10 mL of THF was added 1.185 g (2.67 mmol) of 7. After H$_2$ evolution ceased, 0.67 mL (10.67 mmol) of CH$_3$I was added, followed by Bu$_4$NI (TBAI) (10 mg, 0.030 mmol). After 4 hours, the reaction was quenched by addition of 2 mL of MeOH. After concentration under reduced pressure, the residue was treated with 20 mL of water and extracted with CH$_2$Cl$_2$ (3×30 mL). The organic layer was dried over Na$_2$SO$_4$. After concentration, a colorless oil (1.22 g) was obtained. To a solution of the above crude product (1.22 g, 2.67 mmol) in 10 mL of THF was added 5.3 mL of Bu$_4$NF (a 1 M solution in THF). After the mixture was stirred at room temperature for 2 hours, and then concentrated, giving a residue that was treated with water and extracted with Et$_2$O (3×30 mL). The organic layer was dried over Na$_2$SO$_4$. After concentration and purification by chromatography on silica gel (elution with 30% EtOAc/PE), 0.75 g of 8 (93% for two steps) was obtained as a white solid. $^1$H NMR (300 MHz, CDCl$_3$) δ3.77 (q, 2H), 3.57–3.40 (m, 8H), 2.66 (t, J=5.5 Hz, 1H, OH), 1.80 (q, 2H), 1.56 (m, 2H), 1.26 (s, 28H), 0.88 (t, J=5.5 Hz, 3H, CH$_3$). $^{13}$C-NMR (CDCl$_3$, 75 MHz): δ79.70, 72.67, 72.00, 60.56, 57.83, 34.70, 32.19, 29.87, 29.73, 29.63, 26.38, 22.96, and 14.39.

4-O-Hexadecyl-3-O-methyl-1-iodobutane (9). To a solution of alcohol 8 (0.748 g, 2.17 mmol) in toluene (20 mL) was added Ph$_3$P (0.684 g, 2.61 mmol) and imidazole (0.325 g, 4.18 mmol), followed by iodine (0.717 g, 2.83 mmol). The mixture was heated at reflux (120° C.) for 1 hour. The reaction was cooled and filtered through Celite. The filtrate was concentrated and the residue was purified by chromatography on silica gel (eluting with 5% EtOAc/PE) to afford 0.73 g (75%) of product 9; mp 27–28° C.; [α]$^{23}$−16.67° (c 6.0, CHCl$_3$). $^1$H NMR (300 MHz, CDCl$_3$) δ3.44–3.38 (m, 8H), 3.28 (m, 2H), 2.00 (q, 2H), 1.59 (m, 2H), 1.25 (s, 28H), 0.88 (t, J=6.6 Hz, 3H, CH$_3$). $^{13}$C-NMR (CDCl$_3$, 75 MHz): δ79.92, 72.08, 72.03, 58.27, 36.37, 32.21, 29.99, 29.77, 29.65, 26.43, 22.99, 14.41.

1-S-Acetyl-2-acetamido-3,4,6-tri-O-acetyl-2-deoxy-β-D-glucopyranose (11). After a mixture of 2-acetamido-2-deoxy-D-glucose 10 (2.0 g, 9.04 mmol) and acetyl chloride (3 mL) was stirred overnight, 30 mL of chloroform was added, and the solution was poured into 20 mL of ice water. The mixture was rapidly shaken, the organic layer was run into saturated sodium bicarbonate solution containing cracked ice, and the mixture was stirred at first, then shaken until the acid was neutralized. The chloroform layer was separated and dried over anhydrous Na$_2$SO$_4$. The solution was concentrated in vacuo to afford 2.88 g of a yellow solid, which was used in the next step without purification. A mixture of the above crude product (2.0 g, 5.46 mmol), potassium thioacetate (0.624 g, 5.5 mmol), and dry acetone (20 mL) was shaken for 6 hours. The solution was filtered to remove inorganic material, and the combined filtrate and chloroform washings were concentrated. The residue was purified by chromatography on silica gel (elution with 5% EtOH/CHCl$_3$) to afford 2.04 g (92%) of product 11. $^1$H NMR (300 MHz, CDCl$_3$):δ6.01(d, J=9.9 Hz, 1H, NH), 5.18–5.06 (m, 3H), 5.35 (q, 1H), 4.23 (dd, J=4.4, 12.5 Hz, 1H), 4.05 (dd, J=2.2, 12.4 Hz, 1H), 3.77 (m, 1H), 2.35 (s, 3H, SAc), 2.05 (s, 3H, OAc), 2.02 (s, 6H, OAc), 1.90 (s, 3H, NAc).

3(S)-(3-O-Methyl-4-O-hexadecyl-1-butylthio)-2-acetamido-3,4,6-tri-O-acetyl-2-deoxy-δ-D-glucopyranoside (12). To a degassed solution of 0.60 g (1.476 mmol) of thioacetate 11 in 3 mL of DMF was added NH$_2$NH$_2$,HOAc (0.14 g, 1.48 mmol). The solution was degassed at room temperature for 1 hour. Iodide 9 (0.67 g, 1.47 mmol) was added, followed by triethylamine (0.24 mL, 1.47 mmol).

After 5 hours, 40 mL of EtOAc and 20 mL of H₂O were added. The organic layer was washed with water and brine, and dried over sodium sulfate. After evaporation of the organic solvent, the residue was purified by chromatography on silica gel (eluting with 50% EtOAc/hexane) to afford 0.874 g (87%) of β-thioglycoside 12 as a white solid; mp 129–131° C. [α]$_D^{23}$ –36.92° (c 6.5, CHCl₃). MS: m/z 712 (M⁺+Na⁺), (calcd. C₃₅H₆₃O₁₀NS, 689). ¹H NMR (300 MHz, CDCl₃): δ5.77 (d, J=9.5 Hz, 1H, NH), 5.12 (m, 2H), 4.58 (d, J=10.6 Hz, 1H, H-1), 4.20 (dd, 1H), 4.11 (m, 2H), 3.69 (m, 1H), 3.45–3.37 (m, 8H), 2.79 (m, 2H), 2.05 (s, 3H, OAc), 2.00 (s, 3H, OAc), 1.99 (s, 3H, OAc), 1.92 (s, 3H, NAc), 1.76 (m, 2H), 1.53 (m, 2H), 1.22 (s, 26H), 0.85 (t, J=6.2 Hz, 3H, CH₃). ¹³C-NMR (CDCl₃, 75 MHz): δ170.99, 170.61, 169.99, 169.26, 84.59, 78.78, 76.09, 74.11, 72.53, 71.92, 68.73, 62.55, 57.91, 53.51, 32.12, 32.07, 29.90, 29.70, 29.56, 26.51, 26.36, 23.45, 22.90, 20.92, 20.82, 14.33.

3(S)-(3-O-Methyl-4-O-hexadecyl-1-butylthio)-2-acetamido-4,6-O-benzylidene-2-deoxy-β-D-glucopyranoside (13). To a solution of acetate 12 (0.205 g, 0.297 mmol) in 2 mL of EtOH/CH₂Cl₂ (9:1) was added 36 mg (0.3 mmol) of guanidine hydrochloride, which was prewashed with basic ionic exchange resin. The mixture was stirred at room temperature for 20 minutes, then filtered and washed with EtOH to afford 0.13 g of a white solid. To a solution of the above solid (0.121 g, 0.214 mmol) in 1 mL of DMF was added PhCH(OMe)₂ (98 μL, 0.63 mmol), followed by p-TsOH (4 mg, 0.021 mmol). After the mixture was stirred overnight at room temperature, the reaction was quenched with saturated aqueous NaHCO₃ solution, and extracted with CH₂Cl₂. The organic layer was washed with water and brine, and dried over sodium sulfate. After evaporation of the organic solvents, the residue was purified by chromatography on silica gel (eluting with 50% EtOAc/hexane) to afford 0.123 g (90%) of β-thioglycoside 13 as a white solid; [α]$^{23}$ –63.68° (c 9.5, CHCl₃). ¹H NMR (300 MHz, CDCl₃): δ7.50–7.47 (m, 2H), 7.37–7.34 (m, 3H), 5.88 (d, J=7.0 Hz, 1H, NH), 5.54 (s, 1H), 4.70 (d, J=10.2 Hz, 1H, H-1), 4.32 (dd, J=5.8, 10.2 Hz, 1H, H-2), 3.97 (m, 2H), 3.75 (m, 2H), 3.61–3.35 (m, 10H), 2.82 (m, 2H), 2.04 (s, 3H, NAc), 1.82 (m, 2H), 1.57 (m, 2H), 1.25 (s, 26H), 0.88 (t, J=6.6 Hz, 3H, CH₃). ¹³C-NMR (CDCl₃, 75 MHz): δ171.74, 137.31, 129.26, 128.35, 126.50, 101.86, 84.61, 81.60, 78.83, 77.44, 77.41, 76.94, 73.07, 72.49, 71.96, 70.68, 68.67, 57.92, 56.46, 32.15, 30.36, 30.22, 29.92, 29.74, 29.59, 26.64, 26.38, 23.65, 22.92, 14.37.

3(S)-(3-O-Methyl-4-O-hexadecyl-1-butylsulfonyl)-2-acetamido-4,6-O-benzylidene-3-O-(tert-butyidimethylsilyl)-2-deoxy-β-D-glucopyranoside (14). To a solution of thioglycoside 13 (0.12 g, 0.185 mmol) in 2 mL of DMF was added TBDMSCI (0.096 g, 0.55 mmol), followed by imidazole (0.056 g, 0.83 mmol). The mixture was stirred at room temperature for 5 hours, then filtered and rinsed with CH₂Cl₂. The solution was concentrated and purified by column chromatography on silica gel (elution with 20% EtOAc-PE) to afford 0.65 g (93%) of thioglycoside 14 as a colorless oil; [α]$^{23}$ –42.60° (c 10.0, CHCl₃). ¹H NMR (300 MHz, CDCl₃): δ7.45–7.43 (m, 2H), 7.34–7.32 (m, 3H), 5.77 (d, J=8.8 Hz, 1H, NH), 5.47 (s, 1H), 4.88 (m, 1H), 4.31 (m, 1H), 4.10 (m, 1H), 3.75–3.32 (m, 12H), 2.80 (m, 2H), 1.98 (s, 3H, NAc), 1.78 (m, 2H), 1.54 (m, 2H), 1.24 (s, 26H), 1.02–0.84 (m, 12H), 0.01 (s, 3H, CH₃), –0.05 (s, 3H, CH₃). ¹³C-NMR (CDCl₃, 75 MHz): δ169.98, 137.30, 129.09, 128.19, 126.41, 102.00, 84.44, 82.54, 78.72, 73.13, 72.60, 71.91, 70.63, 68.87, 57.92, 57.85, 32.15, 29.94, 29.74, 29.59, 26.65, 26.39, 26.13, 25.98, 23.98, 22.93, 18.37, –3.77, –4.59.

A solution of MMPA (0.166 g, 0.336 mmol) in H₂O (1 mL) was added to a solution of the above sulfide (0.128 g, 0.168 mmol) in EtOH (1 mL) and THF (1 mL). The mixture was stirred at 55° C. for 1 hour, then concentrated in vacuo to dryness. The residue was treated with 20 mL of saturated aqueous NaHCO₃ solution, and extracted with EtOAc (20 mL×3), dried over Na₂SO₄, and evaporated to dryness. The residue was purified by chromatography on silica gel (elution with 50% EtOAc/PE) to afford 1.11 g (95%) of pure sulfone 14 as a white solid; mp 50–53° C. [α]$^{23}$ –13.00° (c 5.0, CHCl₃). ¹H NMR (CDCl₃, 300 MHz): δ7.46–7.43 (m, 2H), 7.34–7.33 (m, 3H), 6.33 (d, J=7.3 Hz, 1H, NH), 5.48 (s, 1H), 5.28 (m, 1H), 4.57 (t, 1H), 4.32 (m, 1H), 3.77–3.66 (m, 2H), 3.52–3.41 (m, 8H), 3.35–3.19 (m, 2H), 1.97 (m+s, 5H), 1.55 (m, 2H), 1.25 (s, 26H), 0.89–0.82 (m, 12H), 0.01 (s, 3H), –0.05 (s, 3H). ¹³C-NMR (CDCl₃, 75 MHz): δ171.50, 137.00, 129.22, 128.24, 126.41, 102.13, 86.43, 82.02, 78.07, 78.03, 77.37, 72.04, 70.99, 70.71, 68.43, 57.79, 53.92, 46.66, 32.18, 30.32, 30.27, 30.25, 29.94, 29.76, 29.60, 26.38, 25.99, 23.96, 23.59, 22.95, 18.42, 14.38, –3.95, –4.63.

(3S)-3-O-Methyl-4-O-hexadecyl 2'-acetamido-4', 6'-O-benzylidene-3'-O-(tert-butyidimethylsilyl)-2'-deoxy-D-glucopyranosylidenebutane (15). To a solution of 0.12 g (0.15 mmol) of 14 in 1.5 mL of t-BuOH and 2 mL of CF₂BrCF₂Br was added 0.3 g (25% by weight) of KOH/Al₂O₃ (prepared one day earlier). The mixture was heated at 47° C. overnight. The solution was filtered through a pad of Celite, which was washed with CH₂Cl₂. The residue was purified by column chromatography on silica gel (elution with 40% EtOAc-PE) to afford 0.056 g (70%, Z isomer only) of 15 as a colorless oil. MS: m/z 754 (M⁺Na⁺), (calcd. C₄₂H₇₃O₇NSi, 731). ¹H NMR (500 MHz, CDCl₃), δ7.48–7.45 (m, 2H), 7.37–7.34 (m, 3H), 5.54 (s, 1H), 5.38 (d, J=9.3 Hz, 1H, NH), 4.88 (t, J=6.8 Hz, 1H, vinyl H), 4.62 (t, J=8.8 Hz, 1H, H-2), 4.38 (dd, J=5.1, 10.5 Hz, 1H, H-6), 3.80 (t, J=10.3 Hz, 1H, H-6), 3.63 (m, 2H), 3.43–3.34 (m, 9H), 2.45 (m, 1H), 2.24 (m, 1H), 2.05 (s, 3H, NAc), 1.57 (m, 2H), 1.25 (s, 24H), 0.87 (t, J=6.6 Hz, 3H, CH₃), 0.82 (s, 9H). 0.03 (s, 3H, CH₃), –0.04 (s, 3H, CH₃). ¹³C-NMR (CDCl₃, 75 MHz): δ169.46, 150.38, 137.15, 129.19, 128.25, 126.41, 105.65, 102.09, 82.26, 79.83, 74.59, 72.63, 71.96, 70.64, 68.95, 57.48, 54.59, 32.19, 29.96, 29.79, 29.63, 26.43, 26.33, 25.91, 23.84, 22.96, 18.37, 14.39, –3.66, –4.54.

(3S)-3-O-Methyl-4-O-hexadecyl 2'-acetamido-4', 6'-O-hydroxyl-3'-O-(tert-butyldimethylsilyl)-2'-deoxy-β-D-glucopyranosylbutane (16). To a solution of 30 mg (0.041 mmol) of 15 in 5 mL of EtOAc was added 20 mg of 10% Pd/C. After the flask was degassed under H₂ three times, the mixture was stirred overnight under H₂ at room temperature. After filtration of the catalyst, washing with EtOAc, and evaporation of the solvent in vacuo, 23 mg (85%) of 16 was obtained. MS: m/z 668 (M⁺+Na⁺), (calcd. C₃₅H₇₁O₇NSi, 645). ¹H-NMR (400 MHz, CDCl₃), δ5.23(d, J=8.3 Hz, 1H, NH), 3.85 (m, 1H, H-6), 3.71 (m, 1H, H-6), 3.59 (m, 2H), 3.49–3.28 (m, 14H), 2.20 (t, 1H, OH), 2.10 (d, 1H, OH), 1.97 (s, 3H, NAc), 1.68 (m, 2H), 1.55 (m, 2H), 1.24 (s, 26H), 0.88 (s, 12H), 0.11 (s, 3H), 0.07 (s, 3H). ¹³C-NMR (CDCl₃, 75 MHz): δ169.82, 79.82, 79.00, 78.50, 77.57, 72.85, 71.95, 63.20, 57.56, 56.77, 32.19, 29.96, 29.91, 29.77, 27.79, 27.72, 26.39, 26.05, 24.06, 22.96, 18.42, 14.39, –3.55, –4.09.

(3S)-3-O-Methyl-4-O-hexadecyl 2'-acetamido-2'-deoxy-β-D-glucopyranosylbutane (17).

To a solution of 16 (30 mg, 0.046 mmol) in 1 mL of CH₃CN was added BF₃Et₂O (20 μL) at 0° C. After 1 hour, saturated aqueous NaHCO₃ solution was added, followed by extraction with EtOAc (2×20 mL). The organic layer was dried over $Na_2SO_4$ and evaporated to dryness. The residue was purified by chromatography on silica gel (elution with 5:1 $CHCl_3/MeOH$) to afford 23 mg (94%) of 17 as a white solid; mp 146–149° C. $[\alpha]$–11.18° (c 11, $CHCl_3$:MeOH 1:1). MS: m/z 554 ($M^+ + Na^+$), (calcd. $C_{29}H_{57}O_7N$, 531). $^1H$ NMR ($CDCl_3$ and a few drops of MeOH-$d_4$, 300 MHz): $\delta 7.99$(d, J=8.4 Hz, 1H, NH), 3.80 (dd, J=2.8, 12.1 Hz, 1H, H-6), 3.67 (dd, J=4.7, 12.1 Hz, 1H, H-6), 3.55 (t, J=7.7 Hz, 1H), 3.41–3.30 (m, 10H), 3.19 (m, 2H), 2.65 (broad peak), 1.97 (s, 3H, NAc), 1.63–1.49 (m, 6H), 1.21(s, 24H), 0.84(t, J=6.6 Hz, 3H, $CH_3$). $^{13}C$-NMR ($CDCl_3$, 75 MHz): $\delta 172.27$, 79.88, 79.31, 78.26, 77.09, 72.79, 71.97, 71.79, 62.59, 57.50, 55.98, 32.12, 30.01, 29.90, 29.69, 29.55, 27.84, 27.67, 26.29, 23.15, 22.88, 14.29.

(3S)-3-O-methyl-4-O-hexadecyl-2'-amino-2'-deoxy-$\beta$-D-glucopyranosylbutane (4). N-Acetyl-$\beta$-C-glycoside 17 (20 mg, 0.0377 mmol) was dissolved in 2 mL of 2 N KOH/EtOH. After the mixture was degassed and heated at reflux under $N_2$ at 120° C. for 6 hours, the reaction was quenched with 5 mL of saturated $NH_4Cl$ solution, then extracted with $CHCl_3$ (3×20 mL). The organic layer was dried over $Na_2SO_4$ and evaporated to dryness. The residue was purified by chromatography on silica gel (eluting with 5:1 $CHCl_3$/MeOH) to afford 13 mg (74%) of 4 as a white solid; $[\alpha]^{23}$–4.67° (c 6.0, $CHCl_3$:MeOH 2:1). $^1H$ NMR ($CDCl_3$ and a few drops of MeOH-$d_4$, 300 MHz): $\delta 3.73$(m, 1H), 3.66–3.17 (m, 14H), 2.52 (broad peak), 1.72–1.1.45 (m, 6H), 1.20 (s, 24H), 0.81 (t, J=6.5 Hz, 3H). $^{13}C$-NMR ($CDCl_3$ and a few drops of MeOH-$d_4$, 75 MHz): $\delta 79.91$, 79.66, 77.50, 77.42, 76.44, 72.75, 71.90, 71.10, 62.24, 57.69, 32.03, 29.81, 29.69, 29.47, 27.40, 26.91, 26.18, 22.81, 14.17.

EXAMPLE 2

Anti-Proliferative Effects: Cancer Cell Proliferation Study

In this study, the anti-proliferative effects of each of four glucosyl ether lipid compounds were assessed on a panel of epithelial cancer cell lines. Two C-glucosyl ether lipids in accordance with the invention (compounds 4 and 17) were evaluated. In addition, a 2'-deoxy C-glucosyl ether lipid (compound 2) and a 2'-amino-2'-deoxy O-glucosyl ether lipid (compound 3), were evaluated. Thirty mM stock concentration of each of the four compounds were prepared in ethanol.

Figure 2:
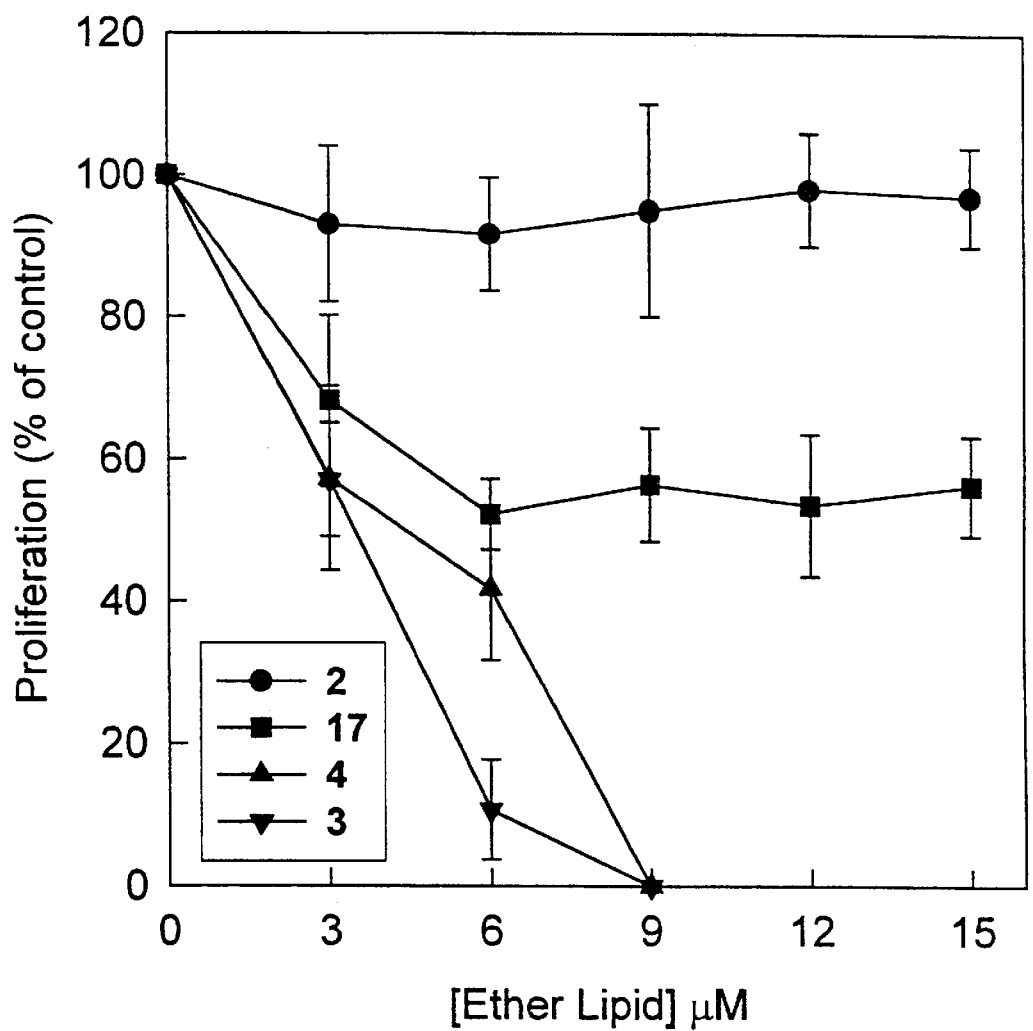
FIG. 2 is a graphical depiction of the results of an anti-proliferation evaluation of two compounds in accordance with the invention (compounds 17 and 4) and two comparative compounds against the neuroblastoma cell line SK-N-SH.
Figure 3:
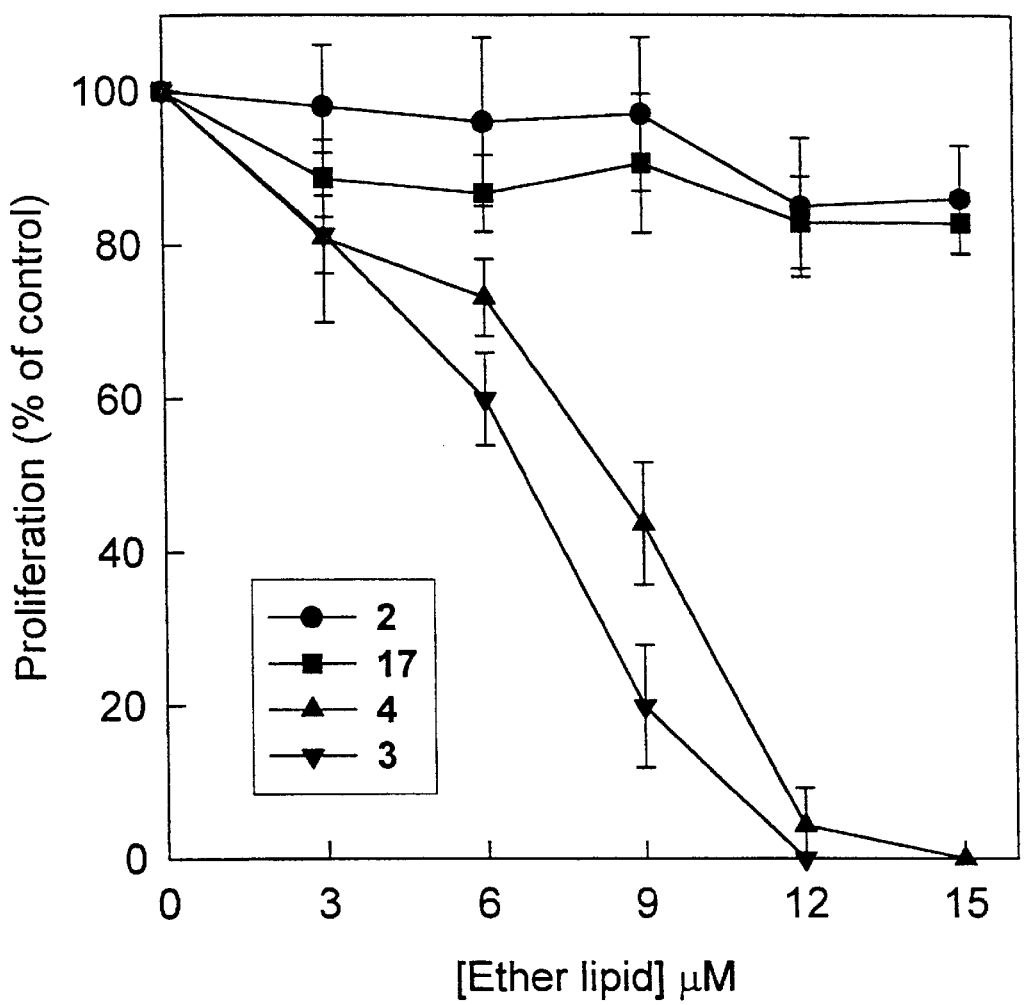
FIG. 3 is a graphical depiction of the results of an anti-proliferation evaluation of two compounds in accordance with the invention (compounds 17 and 4) and two comparative compounds against the prostate cancer cell line DU145.
Figure 4:
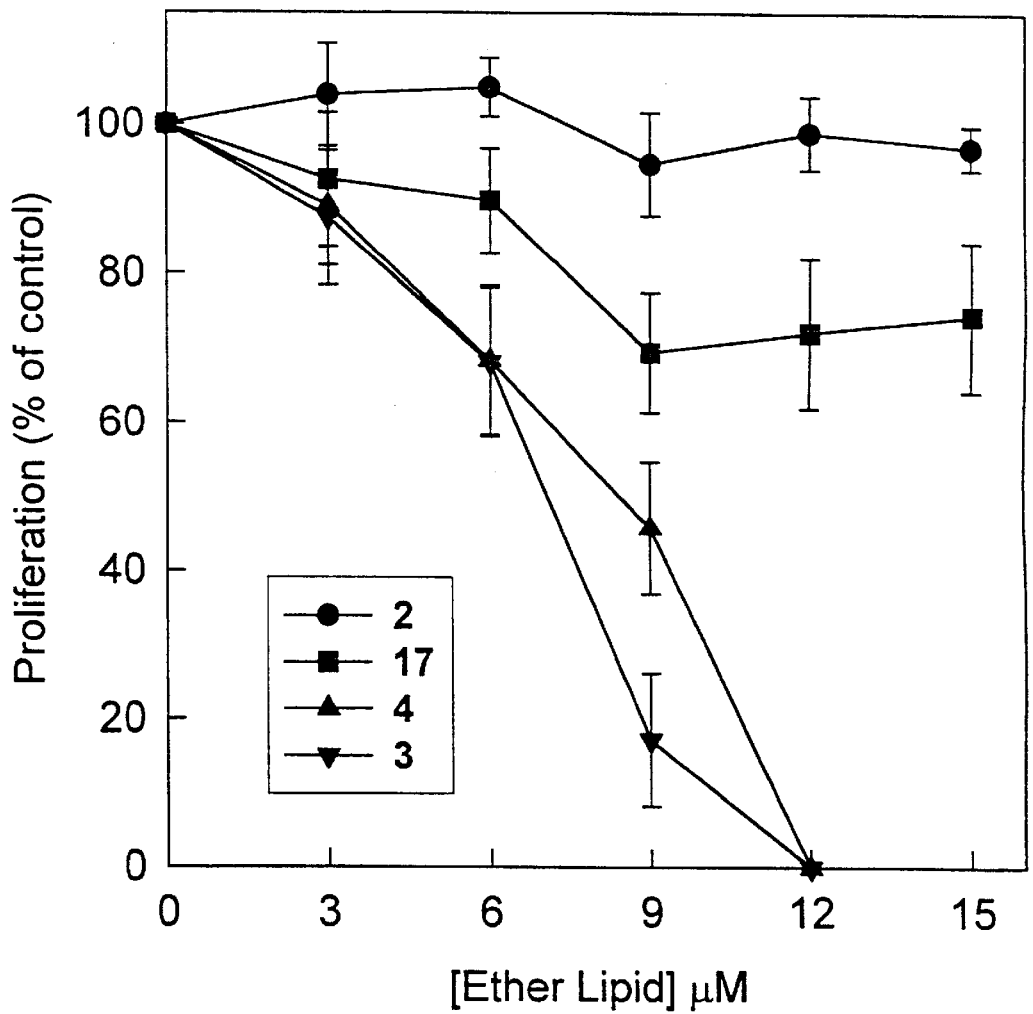
FIG. 4 is a graphical depiction of the results of an anti-proliferation evaluation of two C-glucosyl ether lipid compounds in accordance with the invention (compounds 4 and 17), a 2'-deoxy C-glucosyl ether lipid (compound 2) and a 2'-amino-2'-deoxy O-glucosyl ether lipid (compound 3) against the kidney cancer cell line A498.
Figure 5:
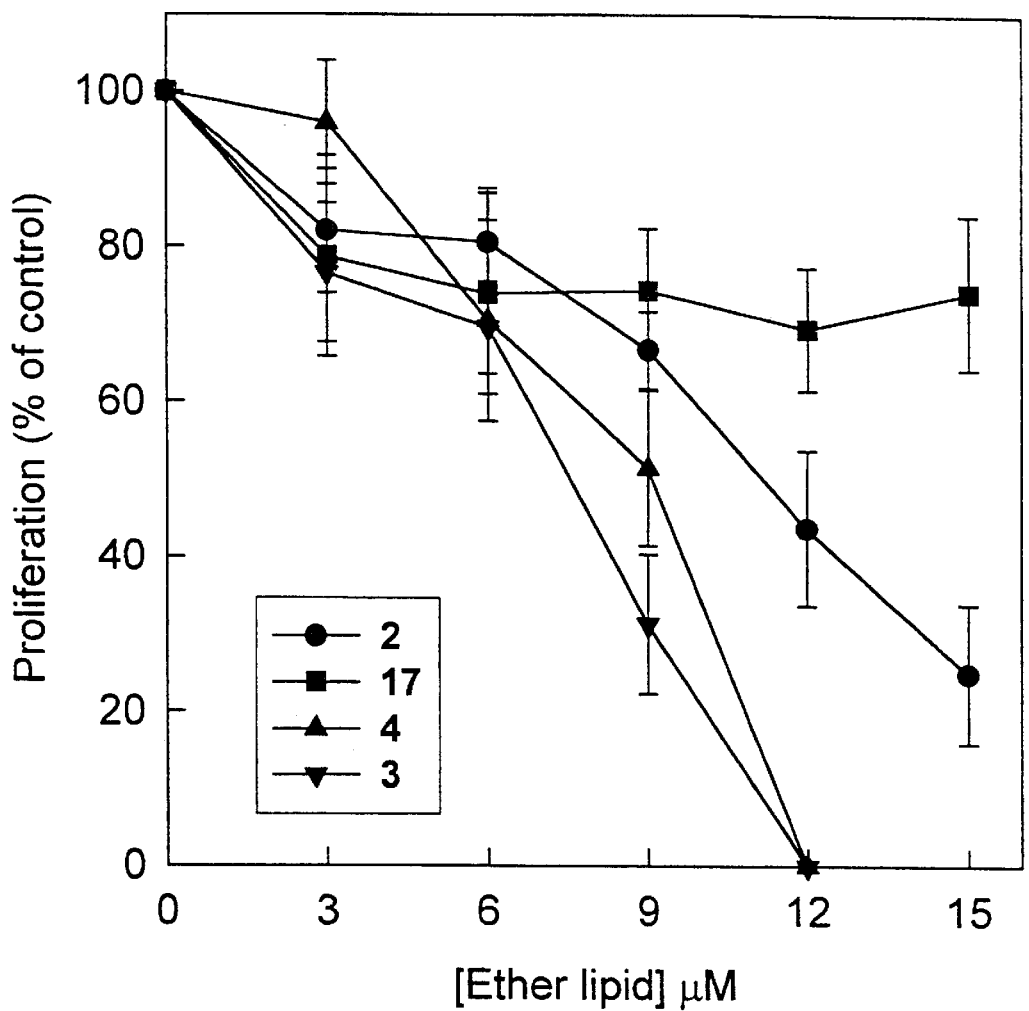
FIG. 5 is a graphical depiction of the results of an anti-proliferation evaluation of two C-glucosyl ether lipid compounds in accordance with the invention (compounds 4 and 17), a 2'-deoxy C-glucosyl ether lipid (compound 2) and a 2'-amino-2'-deoxy O-glucosyl ether lipid (compound 3) against the breast cancer cell line MDA-MB468.
Figure 6:
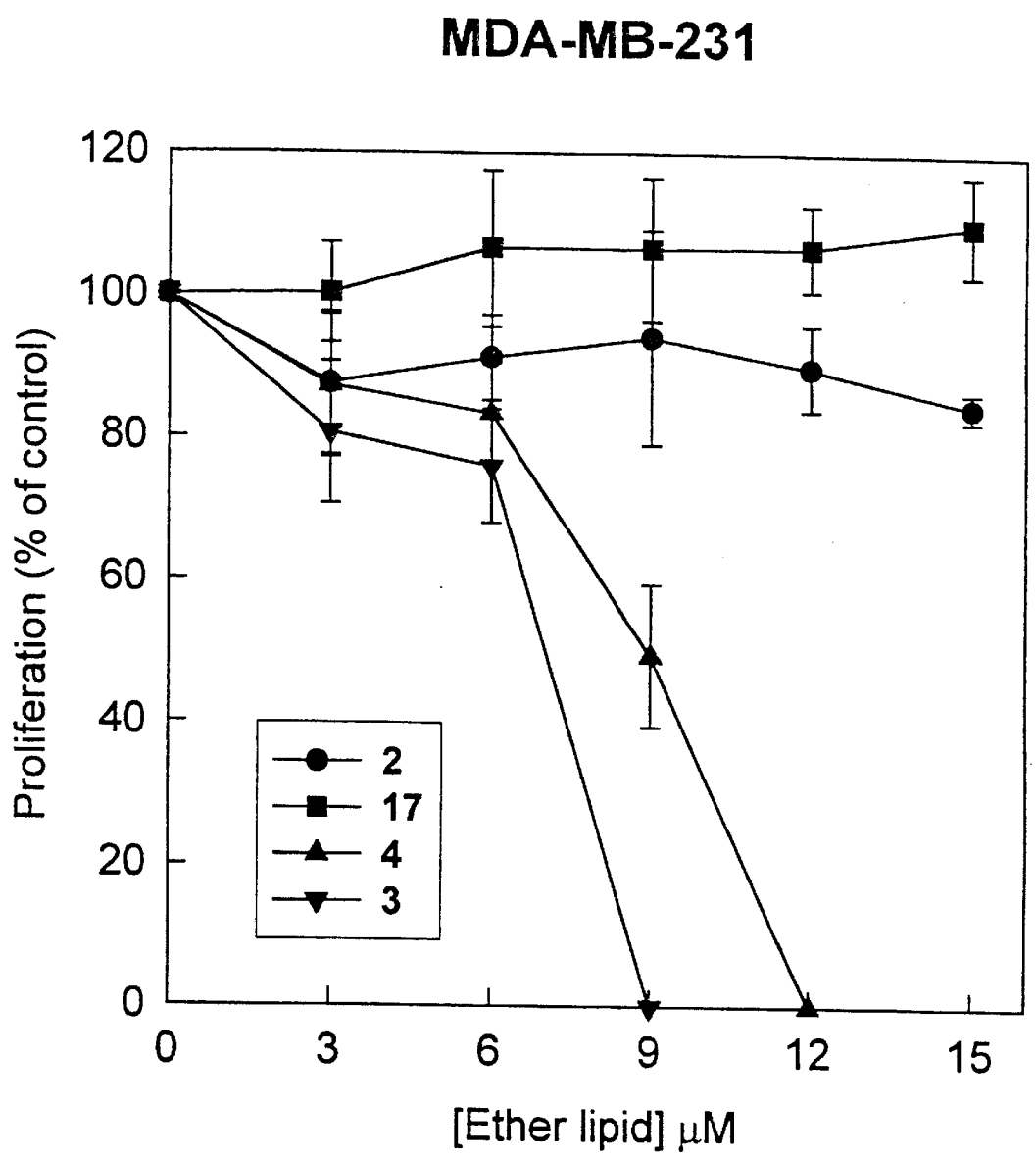
FIG. 6 is a graphical depiction of the results of an anti-proliferation evaluation of two C-glucosyl ether lipid compounds in accordance with the invention (compounds 4 and 17), a 2'-deoxy C-glucosyl ether lipid (compound 2) and a 2'-amino-2'-deoxy O-glucosyl ether lipid (compound 3) against the breast cancer cell line MDA-MB-231.
Figure 7:
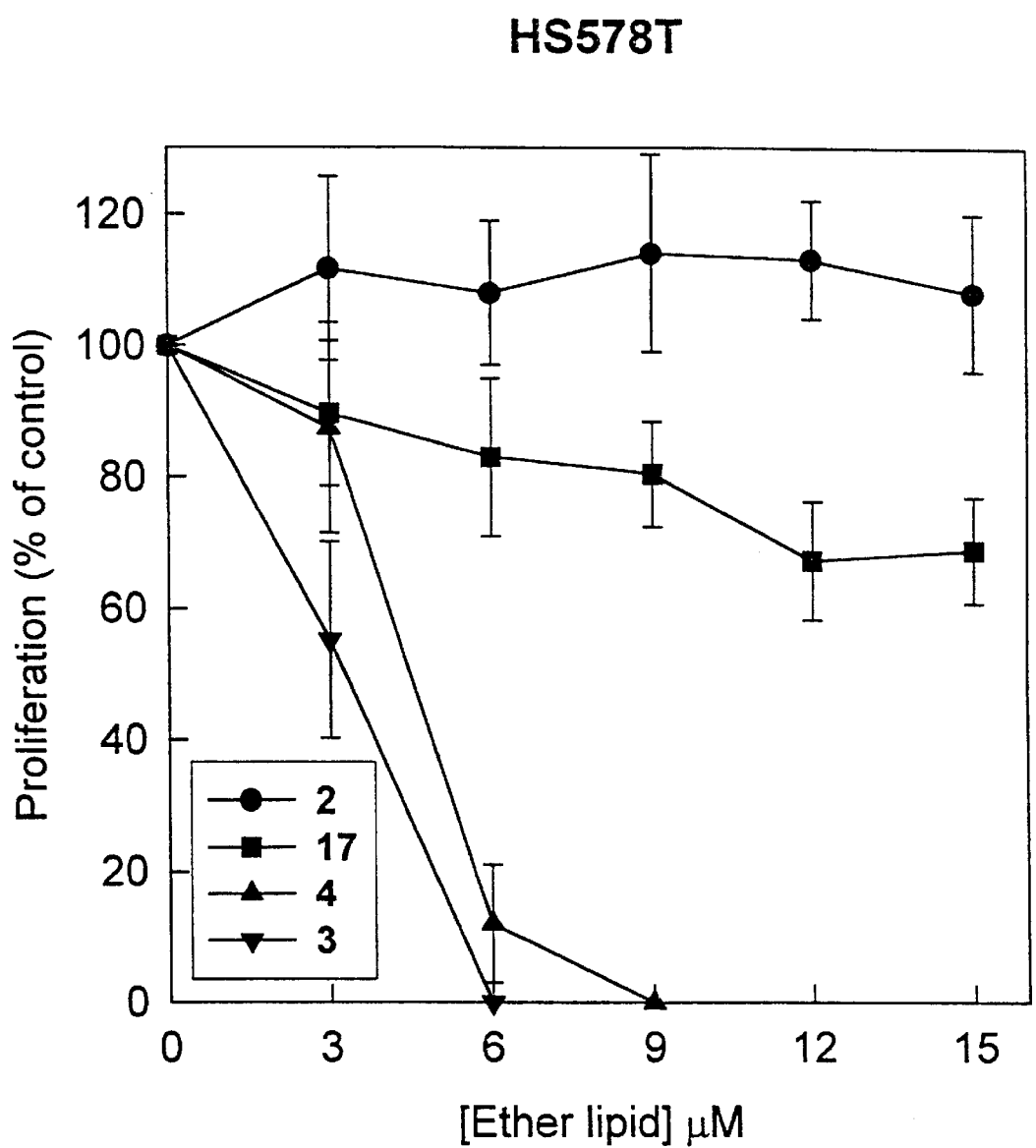
FIG. 7 is a graphical depiction of the results of an anti-proliferation evaluation of two C-glucosyl ether lipid compounds in accordance with the invention (compounds 4 and 17), a 2'-deoxy C-glucosyl ether lipid (compound 2) and a 2'-amino-2'-deoxy O-glucosyl ether lipid (compound 3) against the breast cancer cell line HS578t.
Figure 8:
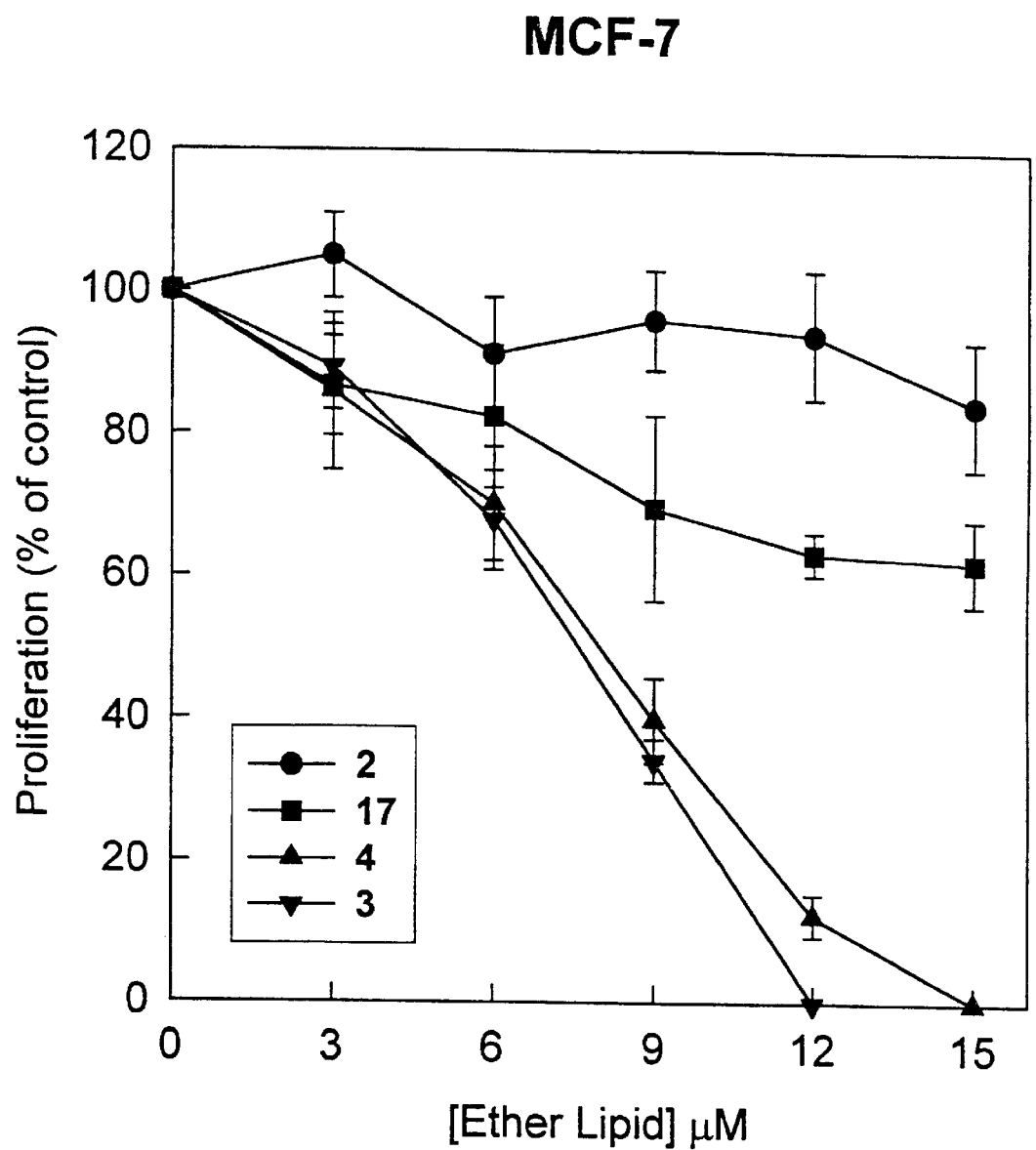
FIG. 8 is a graphical depiction of the results of an anti-proliferation evaluation of two C-glucosyl ether lipid compounds in accordance with the invention (compounds 4 and 17), a 2'-deoxy C-glucosyl ether lipid (compound 2) and a 2'-amino-2'-deoxy O-glucosyl ether lipid (compound 3) against the breast cancer cell line MCF-7.
Figure 9:
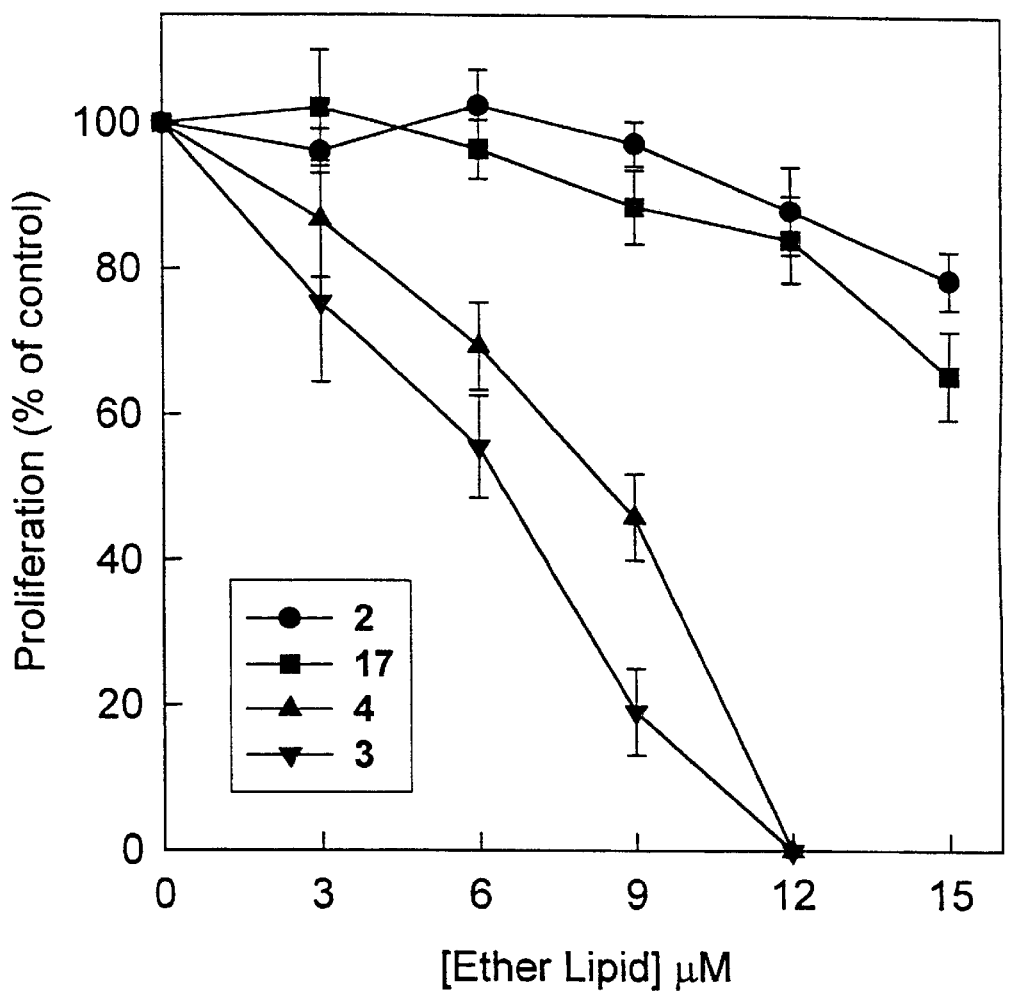
FIG. 9 is a graphical depiction of the results of an anti-proliferation evaluation of two C-glucosyl ether lipid compounds in accordance with the invention (compounds 4 and 17), a 2'-deoxy C-glucosyl ether lipid (compound 2) and a 2'-amino-2'-deoxy O-glucosyl ether lipid (compound 3) against the breast cancer cell line BT549.

The experimental procedure used is detailed in Lu, X. and Arthur, G., *Cancer Res.*, 52:2806–2812 (1992), the pertinent parts of which are incorporated by reference. Briefly, the epithelial cancer cell lines, namely SK-N-MC and SK-N-SH (neuroblastoma); DU145 (prostate); A498 (kidney); MDA-MB-468, MDA-MB-231, HS578t, MCF-7 and BT549 (breast), were subcultured into 24-well plates and allowed to grow to exponential phase. The medium was changed and replaced with one containing the glucosyl ether lipid compounds (0–15 M) in 10% FBS-supplemented medium. The cell numbers in representative wells were determined at the time of addition of the compounds. After 48 hours, the cells were detached with trypsin and the numbers were determined with a Coulter Counter. The increase in cell numbers were expressed as a percentage relative to those in wells without any drug (control). The results are graphically presented in FIGS. 1 through 9, which show that the inventive amino-substituted C-glycoside ether lipid 4 exhibited similar anti-proliferative efficacies against the panel of cancer cell lines as its O-glycoside counterpart 3. The inventive N-acetyl substituted C-glycoside 17 and 2-deoxy C-glycoside 2, while exhibiting anti-proliferative effects against several of the cell lines, were generally less efficacious than the other two glycoside ether lipids evaluated.

EXAMPLE 3

Anti-Proliferative Effects: $Gl_{50}$ Study

We now describe an example in which the O- and C-glycerolipids of glucosamine display very similar micromolar antiproliferative activity vs. nine tumor cell lines. Our plan was to compare glucosamine derivatives 3 and 4 since one of us had shown earlier that O-glycoside 3 had micromolar antiproliferative activity in assays against several tumor cell lines. See Erukulla, et al., *J. Med. Chem.*, 39:1545–1548 (1996), the pertinent portions of which are incorporated herein by reference. Table 1 summarizes the comparative test results for 17, 3, 4, and the 2-deoxy analog of 4, (3S)-3-O-methyl-4-O-hexadecyl-2'-deoxy-$\beta$-D-glucopyranosylbutane (compound 2), which had been described in our earlier paper (Yang et al., *Org. Lett.*, 1:2149–2151 (1999)). The method utilized was the same as that described in Example 2 above, and the $Gl_{50}$ values were extrapolated from the results shown in FIGS. 1–9. In all nine examples, the close similarity in antiproliferative activity is striking.

TABLE 1

| Growth inhibitory properties of C-glycolipids versus mammary tumor cells reported as $Gl_{50}$ ($\mu M$) | | | | |
|---|---|---|---|---|
| Cell line | 2 | 3 | 4 | 17 |
| MCF-7, breast | >15 | 8.0 | 8.1 | 25 |
| MDA-MB-468, breast | 11.4 | 7.0 | 9.0 | 34.4 |
| MDA-MB-231, breast | >15 | 7.1 | 9.1 | 40.0 |
| HS578T, breast | >15 | 3.1 | 5.1 | 21 |
| BT549, breast | >15 | 6.5 | 8.9 | 28.5 |
| A498, kidney | >15 | 6.9 | 8.5 | >15 |
| SK-N-SH, neuronal | >15 | 3.8 | 4.1 | >15 |
| SK-N-MC, neuronal | >15 | 4.1 | 4.1 | >15 |
| DU145, prostate | >15 | 6.5 | 7.9 | >15 |

$Gl_{50}$, drug concentration ($\mu M$) required to inhibit growth by 50%. The cells were treated with each compound for 48 hours.

This invention has been described in terms of specific embodiments set forth in detail herein, but it should be understood that these are by way of illustration and the invention is not necessarily limited thereto. Modifications and variations will be apparent from the disclosure and may be resorted to without departing from the spirit of the inventions those of skill in the art will readily understand. Accordingly, such variations and modifications are considered to be within the purview and scope of the invention defined in the following claims.

What is claimed is:
1. A C-glucosyl ether lipid of the formula:

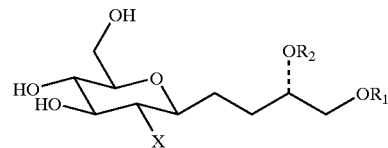

wherein:
$R_1$ is a $C_{12}$–$C_{20}$ alkyl or $C_{12}$–$C_{20}$ alkenyl;
$R_2$ is a $C_1$–$C_3$ alkyl or a $C_3$ cycloalkyl; and
X is a nitrogen-containing group.

2. The C-glucosyl ether lipid of claim 1, wherein $R_1$ is $C_{16}H_{33}$ or $C_{18}H_{37}$.

3. The C-glucosyl ether lipid of claim 1, wherein $R_2$ is a $C_1$–$C_3$ alkyl.

4. The C-glucosyl ether lipid of claim 1, wherein X is $NH_2$, $NHCOR_3$ or $NHSO_2R_4$; such that $R_3$ is a $C_1$–$C_3$ alkyl, and $R_4$ is a $C_1$–$C_3$ alkyl, a phenyl, a substituted phenyl or a substituted naphthyl.

5. The C-glucosyl ether lipid of claim 1, wherein:
   $R_1$ is $C_{16}H_{33}$ or $C_{18}H_{37}$;
   $R_2$ is a $C_1$–$C_3$ alkyl; and
   X is $NH_2$, $NHCOR_3$ or $NHSO_2R_4$; such that $R_3$ is a $C_1$–$C_3$ alkyl, and $R_4$ is a $C_1$–$C_3$ alkyl, a phenyl, a substituted phenyl or a substituted naphthyl.

6. The C-glucosyl ether lipid of claim 1, wherein X is $NH_2$.

7. The C-glucosyl ether lipid of claim 1, wherein $R_1$ is $C_{16}H_{33}$.

8. The C-glucosyl ether lipid of claim 1, wherein $R_2$ is $CH_3$.

9. The C-glucosyl ether lipid of claim 1, wherein $R_1$ is $C_{16}H_{33}$, $R_2$ $CH_3$, and X is $NH_2$.

10. A pharmaceutical composition comprising the C-glucosyl ether lipid of claim 1.

11. A pharmaceutical composition comprising the C-glucosyl ether lipid of claim 5.

12. A pharmaceutical composition comprising the C-glucosyl ether lipid of claim 9.

13. A method of treating an animal afflicted with a cancer, the method comprising administering an anti-cancer effective amount of the pharmaceutical composition of claim 10 to the animal.

14. A method of treating an animal afflicted with a cancer, the method comprising administering an anti-cancer effective amount of the pharmaceutical composition of claim 11 to the animal.

15. A method of treating an animal afflicted with a cancer, the method comprising administering an anti-cancer effective amount of the pharmaceutical composition of claim 12 to the animal.

16. A method of synthesizing a C-glucosyl ether lipid, the C-glucosyl ether lipid having a nitrogen-containing group at the C2 position of the glucose moiety and an O-alkyl or O-cycloalkyl side chain on the sn-2 carbon of the ether lipid moiety, the method comprising:
   a) synthesizing an ether lipid having an sn-2 carbon and an O-alkyl or O-cycloalkyl side chain attached to the sn-2 carbon;
   b) sulfur-linking a glucose derivative to the ether lipid synthesized in step a) to form a thioglycoside intermediate, the glucose derivative having a nitrogen containing group at the C2 position; and
   c) converting the thioglycoside intermediate to a C-glucosyl ether lipid via a Ramberg-Bäcklund rearrangement.

* * * * *